US00PP23824P2

(12) United States Plant Patent
Smith

(10) Patent No.: US PP23,824 P2
(45) Date of Patent: Aug. 13, 2013

(54) ***ARENARIA* PLANT NAMED 'LEMON ICE'**

(50) Latin Name: *Arenaria montana*
Varietal Denomination: Lemon Ice

(75) Inventor: Mark C. Smith, Bellingham, WA (US)

(73) Assignee: Pacific Plug and Liner, Watsonville, CA (US)

( * ) Notice: Subject to any disclaimer, the term of this patent is extended or adjusted under 35 U.S.C. 154(b) by 136 days.

(21) Appl. No.: 13/317,888

(22) Filed: Oct. 31, 2011

(51) Int. Cl.
*A01H 5/00* (2006.01)

(52) U.S. Cl.
USPC ..... Plt./263.1

(58) Field of Classification Search
USPC ..... Plt./263.1, 395
See application file for complete search history.

*Primary Examiner* — Howard Locker
(74) *Attorney, Agent, or Firm* — Penny J. Aguirre

(57) ABSTRACT

A new cultivar of hybrid *Arenaria*, 'Lemon Ice', characterized by its flowers that are lemon yellow in color and open from bright yellow flower buds, and its dense, compact, and spreading plant habit.

2 Drawing Sheets

Botanical classification: *Arenaria montana.*
Cultivar designation: 'Lemon Ice'.

BACKGROUND OF THE INVENTION

The present invention relates to a new and distinct cultivar of *Arenaria montana*, known as 'Lemon Ice' and will be referred to hereafter by its cultivar name, 'Lemon Ice'.

The inventor discovered the new cultivar, 'Lemon Ice', as a naturally occurring branch mutation of 'Avalanche' (not patented) that was growing in field planted with 'Avalanche' in Marysville, Wash. in 2008.

Asexual reproduction of the new cultivar was first accomplished by tip cuttings in Watsonville, Calif. in 2009 under the direction of the Inventor. Repeated asexual reproduction has determined that the characteristics of this cultivar are stable and are reproduced true to type in successive generations.

SUMMARY OF THE INVENTION

The following traits have been repeatedly observed and represent the characteristics of 'Lemon Ice'. These attributes in combination distinguish 'Lemon Ice' as a new and distinct cultivar of *Arenaria.*

1. 'Lemon Ice' exhibits flowers that are lemon yellow in color and open from bright yellow flower buds.
2. 'Lemon Ice' exhibits a dense, compact, and spreading plant habit similar to its parent plant.

'Avalanche', the parent plant, is similar to 'Lemon Ice' in plant habit but differs from 'Lemon Ice' in having white flowers. 'Lemon Ice' can also be compared to the cultivar 'Sapare' (U.S. Plant Pat. No. 21,303). 'Sapare' is similar to 'Lemon Ice' in having a compact form but differs from 'Lemon Ice' in having white flowers. Typical plants of the species, *Arenaria montana*, differ from 'Lemon Ice' in having smaller white flowers and a less compact plant habit.

BRIEF DESCRIPTION OF THE DRAWING

The accompanying colored photographs illustrate the overall appearance and distinct characteristics of the new

*Arenaria*. The photographs were taken of one year-old plants of 'Lemon Ice' as grown outdoors in 2-gallon containers in Watsonville, Calif.

Figure 1:
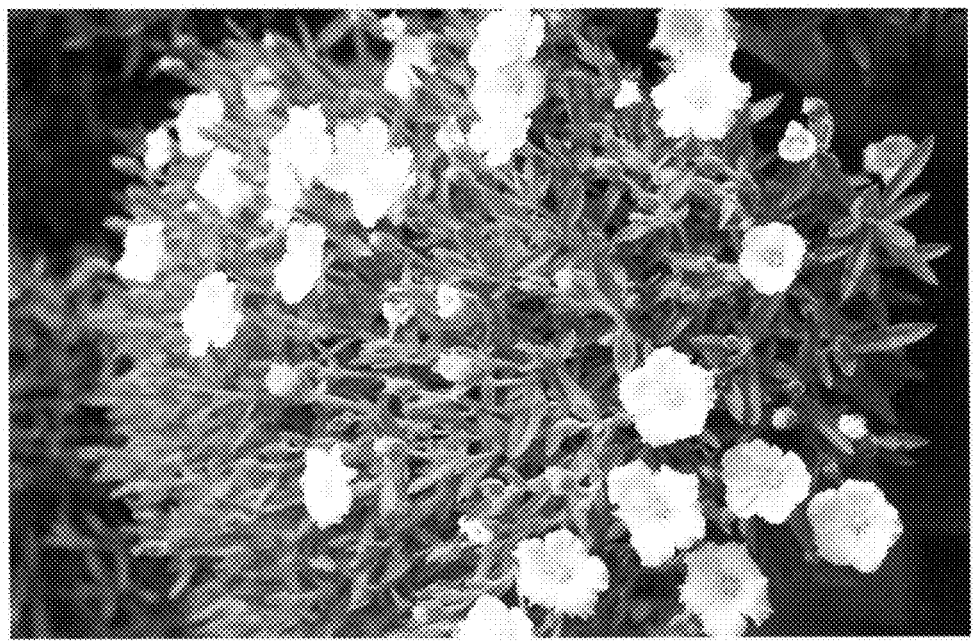

The photograph in FIG. 1 is a top view of a plant of 'Lemon Ice' in bloom.

Figure 2:
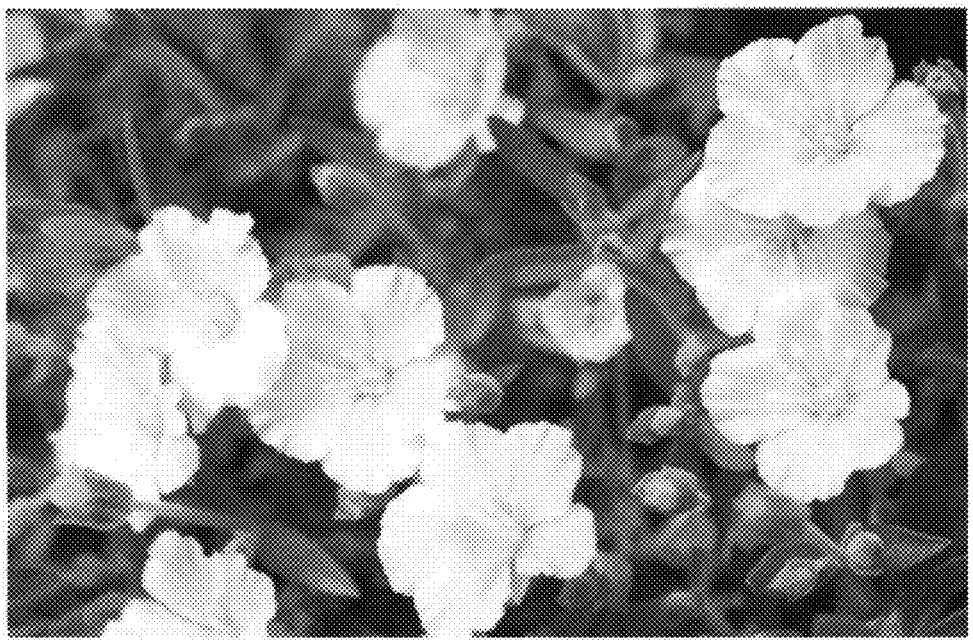

The photograph in FIG. 2 is of a close-up view of the flowers of 'Lemon Ice'.

Figure 3:
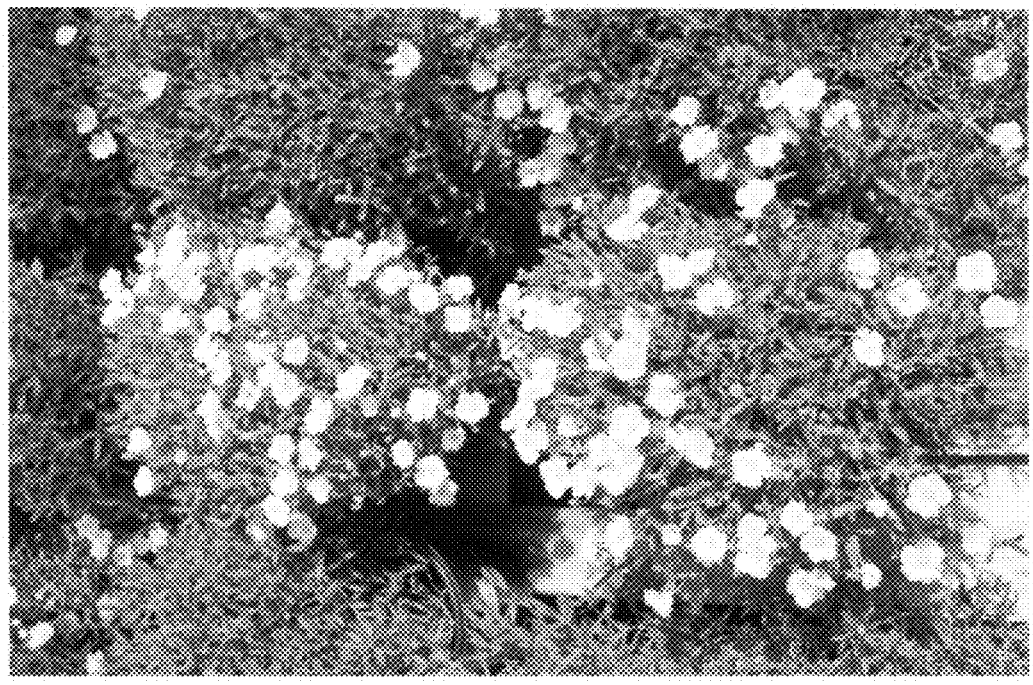

The photograph in FIG. 3 provides a view of the plant habit of 'Lemon Ice'.

Figure 4:
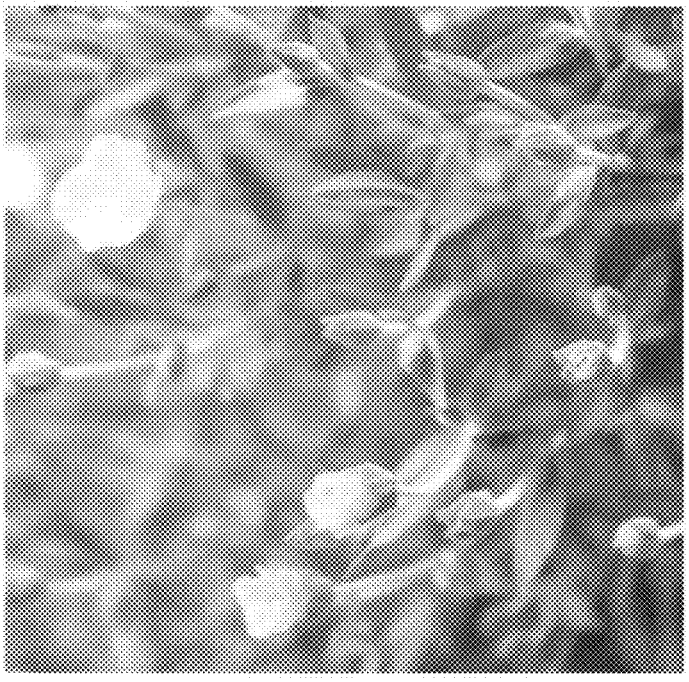

The photograph in FIG. 4 provides a close-up view of the flower buds of 'Lemon Ice'. The colors in the photographs are as close as possible with the digital photography and printing techniques utilized and the color codes in the detailed botanical description accurately describe the colors of the new *Arenaria.*

DETAILED BOTANICAL DESCRIPTION OF THE PLANT

The following is a detailed description of one year-old plants of the new cultivar as grown outdoors in 2-gallon containers in Watsonville, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—May to June in California.

*Plant habit.*—Herbaceous perennial with a dense, compact, upright and spreading plant habit.

*Height and spread.*—Reaches about 20 cm in height and about 30 cm in spread.

*Hardiness.*—At least to U.S.D.A. Zones 3 to 8.

*Diseases and pests.*—No susceptibility or resistance to diseases or pests has been observed.

*Root description.*—Fine and fibrous.

Growth and propagation:

*Growth rate*.—Vigorous.

*Propagation*.—Terminal stem cuttings (tip cuttings).

Stem description:

*Stem size*.—Average of 17 cm in length and 1 mm in width, with lateral branches (about 4 per stem); an average of 6 cm in length and 1 mm in width.

*Stem shape*.—Round.

*Stem color*.—New growth; 145B, mature stems; 161A and 165A at base.

*Stem surface*.—Pubescent.

*Stem aspect*.—Prostrate.

*Internode length*.—Average of 1.5 cm on upper portion for branches, leaf internode length 2 to 8 mm.

*Branching habit*.—Dense basal branches (an estimate of 2,000 in a 2-gallon container) about 4 lateral branches per stem.

Foliage description:

*Leaf shape*.—Lanceolate to narrowly elliptic.

*Leaf division*.—Simple.

*Leaf base*.—Cuneate.

*Leaf apex*.—Acute.

*Leaf venation*.—Not discernable.

*Leaf margin*.—Entire.

*Leaf attachment*.—Sessile.

*Leaf arrangement*.—Opposite.

*Leaf surface*.—Puberulent on upper and lower surface.

*Leaf color*.—Young and mature upper and lower surface; a blend of 137A and 137B.

*Leaf size*.—Up to 2 cm in length and 5 mm in width.

*Leaf quantity*.—Average of 14 per stem length of 5 cm.

*Stipules*.—Two at each node, narrow ovate to narrow deltoid in shape, average of 9 cm in length and 3 mm in width, 183B to 184B.

Flower description:

*Inflorescence type*.—Cyme, terminal flower opens first.

*Lastingness of flowers*.—About 2 weeks.

*Inflorescence size*.—An average of 2 cm in width and 1.5 cm in depth.

*Flower size*.—Average of 2 cm in depth and 1 cm in diameter.

*Flower fragrance*.—None.

*Flower number*.—Average of 3 per cyme, one cyme per lateral branch.

*Flower type*.—Rotate.

*Flower aspect*.—Upright to stem.

*Flower bud*.—Oblong in shape, an average of 6 mm in length and 5 mm in width, 1C in color with the sepal portion 144C in color.

*Petals*.—5, broadly orbicular in shape, round apex, broadly cuneate base, slightly crenate and wavy, an average of 7 mm in length and width, surface is velvety on upper and lower surface, color on upper and lower surface; a blend of 1C, 4C and 4D.

*Calyx form*.—Campanulate.

*Sepals*.—5, ovate in shape, acute apex, broadly cuneate base, entire margins, an average of 5 mm in length and 3 mm in width, 144C in color on upper and lower surface, surface is slightly pubescent on upper and lower surface.

*Peduncles*.—An average of 1.5 cm in length and 1.5 mm in diameter, surface is very slightly pubescent, 145B in color.

*Pedicels*.—An average of 1 cm in length and 1 mm in width, 145B in color, very slightly pubescent surface, slightly ovoid in shape, held upright.

Reproductive organs:

*Gynoecium*.—3 pistils, styles are about 2 mm in length, and 1D in color, stigma is very short and 1D in color, ovary is about 3 mm in diameter, conspicuous, round in shape, and 145B in color.

*Androcoecium*.—An average of 10 stamens, anthers are oval in shape, 0.6 mm in length, and 5D in color, filament is 4 mm in length and 4D in color, pollen is low in quantity 4D in color.

*Fruit/seeds*.—No fruits or seeds observed.

It is claimed:

1. A new and distinct cultivar of *Arenaria* plant named 'Lemon Ice' as herein illustrated and described.

* * * * *